United States Patent [19]

Tardy et al.

[11] Patent Number: 5,618,551
[45] Date of Patent: Apr. 8, 1997

[54] BIOCOMPATIBLE BIORESORBABLE AND NON-TOXIC ADHESIVE COMPOSITION FOR SURGICAL USE

[75] Inventors: Michel Tardy; Jérôme Tiollier, both of Lyons; Jean-Louis Tayot, La Tour De Salvagny, all of France

[73] Assignee: Imedex, Chaponost, France

[21] Appl. No.: 376,185

[22] Filed: Jan. 20, 1995

[30] Foreign Application Priority Data

Jan. 24, 1994 [FR] France ................... 94 00715

[51] Int. Cl.$^6$ ........................ A61L 25/00
[52] U.S. Cl. ............ 424/426; 424/443; 424/444; 424/445; 424/484
[58] Field of Search .................. 424/426, 443, 424/444, 445, 484

[56] References Cited

U.S. PATENT DOCUMENTS

| | | | |
|---|---|---|---|
| 3,949,073 | 4/1976 | Daniels et al. | 424/89 |
| 4,140,537 | 2/1979 | Luck et al. | 106/161 |
| 4,233,360 | 11/1980 | Luck et al. | 428/310 |
| 4,931,546 | 6/1990 | Tardy et al. | 530/356 |
| 5,077,049 | 12/1991 | Dunn et al. | 424/426 |
| 5,081,106 | 1/1992 | Bentley et al. | 424/443 |
| 5,201,745 | 4/1993 | Tayot et al. | 424/444 |
| 5,204,382 | 4/1993 | Wallace et al. | 424/423 |
| 5,308,889 | 5/1994 | Rhee et al. | 604/11 |
| 5,340,849 | 8/1994 | Dunn et al. | 424/78.27 |
| 5,412,076 | 5/1995 | Gagnieu | 424/443 |

FOREIGN PATENT DOCUMENTS

| | | |
|---|---|---|
| 083868 | 7/1983 | European Pat. Off. |
| 089145 | 9/1983 | European Pat. Off. |
| 0253715 | 1/1988 | European Pat. Off. |
| 0466383 | 1/1992 | European Pat. Off. |
| 0575273 | 12/1993 | European Pat. Off. |

OTHER PUBLICATIONS

Snestad et al., *Chemical Abstracts*, vol. 100, 1984, #39644.
Wallace et al., *Chemical Abstracts*, vol. 119, 1993, #415396.
Bentley et al., *Chemical Abstracts*, vol. 116, #181193.
Tsunenaga et al., *Chemical Abstracts*, vol. 113, #29337.
Wallace et al., *Chemical Abstracts*, vol. 99, #93803.

*Primary Examiner*—Thurman K. Page
*Assistant Examiner*—Sharon Howard
*Attorney, Agent, or Firm*—Larson & Taylor

[57] ABSTRACT

The invention relates to a biocompatible, bioresorbable and non-toxic adhesive composition for surgical use, for the bonding, in particular, of biological tissues to one another or in an implanted biomaterial, characterized in that it comprises a reactive acidic solution of non-crosslinked and potentially crosslinkable collagen or gelatin modified by oxidative cleavage, at a concentration which is preferably between approximately 5 and 30 by weight. It also relates to reactive acidic solutions and powders based on non-crosslinked collagen or gelatin modified by oxidative cleavage which are used as intermediate products in the preparation of the above-mentioned composition, and to the process for their preparation. It also relates to adhesive kits which comprise, on the one hand, the above-mentioned reactive acidic solution and, on the other hand, a neutralizing solution and which are intended for extemporaneous mixing. Finally it relates to a method of application of the adhesive, composition according to the invention. The invention is particularly useful in the areas of adhesion, haemostasis, leaktightness with respect to liquids or gases, cicatrization, filling, avoiding adhesion in surgery, embolization, as a local system for release of medicamentary active principles, etc.

26 Claims, 1 Drawing Sheet

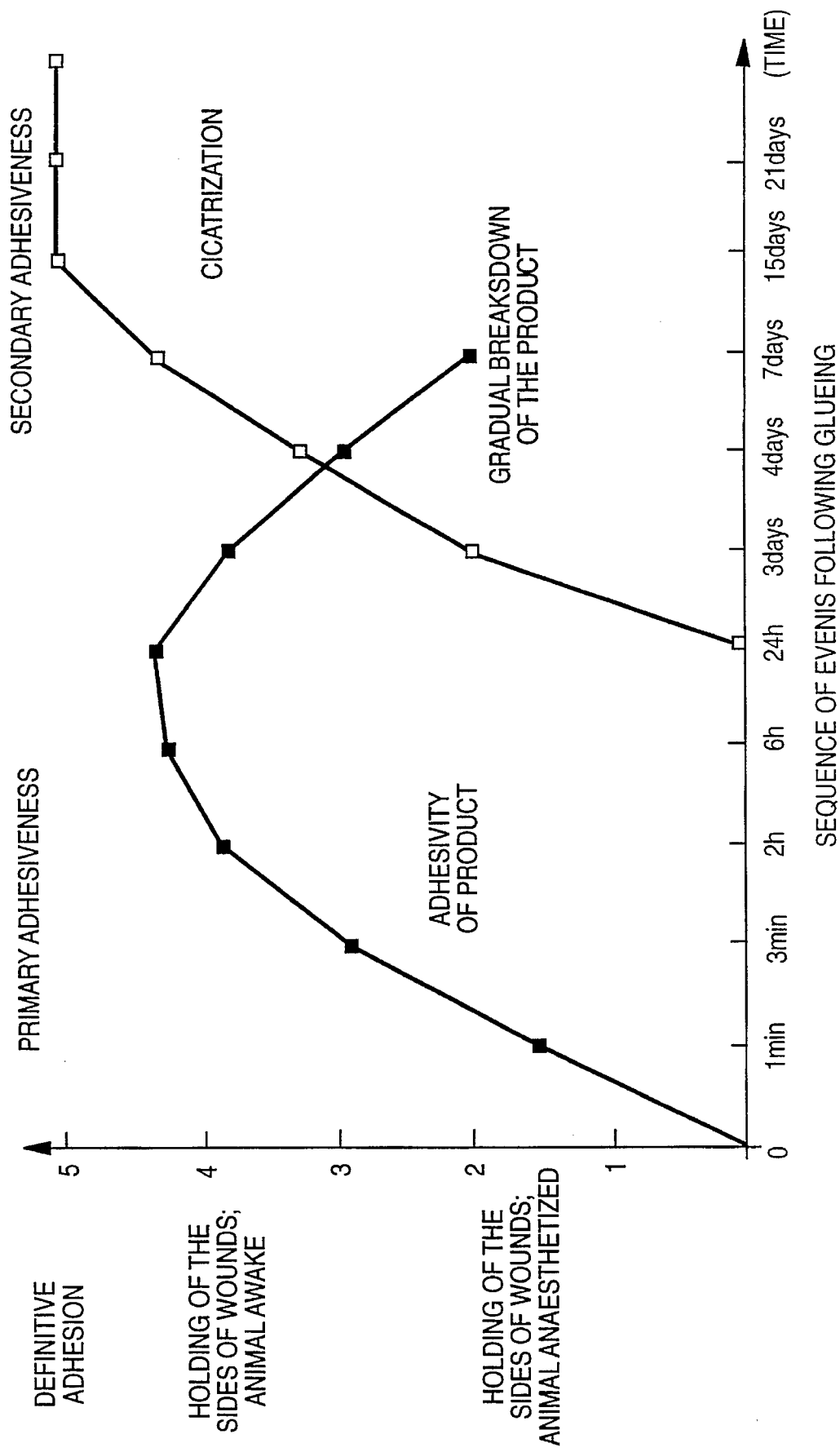

BIOCOMPATIBLE BIORESORBABLE AND NON-TOXIC ADHESIVE COMPOSITION FOR SURGICAL USE

The present invention is in the field of adhesive compositions which are intended for surgical use. The invention relates more precisely to a biocompatible, bioresorbable and non-toxic adhesive composition for the bonding, in particular, of biological tissues, including living tissues, to one another or for the bonding of biological tissues and an implanted biomaterial, which composition is based on non-crosslinked collagen or gelatin modified by oxidative cleavage and soluble in an acidic medium.

The invention also relates to the intermediate products which are used in the preparation of the above-mentioned adhesive compositions and to a process for their preparation and additionally relates to adhesive kits which are intended for extemporaneous surgical use.

The development and use of tissue glues for surgical use has been the subject of much research and numerous experimental studies for some decades.

One known adhesive composition, for example, consists of gelatin, resorcinol and formaldehyde (GRF) and was used between the 1960s and the 1980s. In this composite, the adhesive function is taken by the gelatin, polymerized by the formaldehyde, while the resorcinol (which is a phenol) is used to reduce the dissolution of the adhesive composition. Problems of tissue toxicity as well as of a lack of adhesion have been noted in a number of studies (Braunwald et al., Surgery, 59: 1024–1030 (1966); Bachet et al., J. Thorac. Cardiovasc. Surg., 83: 212–217 (1982)). Moreover, it is no longer possible to consider employing formaldehyde in compositions for surgical use because of the risks posed by the release of this component and by its toxicity.

Also known is an adhesive system which was developed from a polypeptide isolated from the byssus of the mussel (marine adhesive protein) (Waite J. H. et al., Biochem., 24: 5010–5014 (1985)). While originally extracted from the mussel, this protein was subsequently obtained by a synthetic route or by genetic manipulation (see in particular European Patent Application No. 242 656 and International Patent Application WO 88/03953, and Marumo et al., Biochem. Biophys. Acts, 872, 98–103 (1986); Swerdloff M. D. et al., Int. J. Peptide Protein Res., 33, 313 (1989)). It is formed from a chain of repeating units which consist of a characteristic decapeptide rich in hydroxylatable tyrosine and proline residues and comprising DOPA (3,4-dihydroxyphenylalanine) which are responsible for these strong adhesion properties. Although promising at the conceptual level, this adhesive is nevertheless unavailable following difficulties in its development and because of the toxicity of certain forms of decapeptides. This system has been the subject of numerous patents (see in particular International Patent Application WO 92/10567 and the European patent applications published under Nos. 243 818 and 244 688; patents U.S. Pat. Nos. 4,808,702, 4,687,740 and AU-8 824 972).

However, it is in fact the development of a glue based on fibrinogen and thrombin which allowed the fields in which tissue glues are used to be truly developed.

The use of fibrinogen as a biomaterial for adhesive purposes dates from the beginning of the 1940s (Young, Medawar, Lancet II: 126–132 (1940)). After the initial results obtained in nerve anastomoses (Tarlov and Benjamin, Surg. Gynecol. Obstet., 76 366–374 (1943)), this adhesive system was not satisfactory because of the low concentration of fibrinogen in the plasmas employed.

Then, in the 1970s, the idea of a glue was reintroduced by the use of a cryoprecipitate containing high concentrations of fibrinogen (Madras et al., Wien Klin. Wochenschr., 87: 495–501 (1972)). This type of glue was subsequently commercialized by the company Immuno under the name "Tissucol" (Tisseel), then by Behringwerke under the name "Beriplast" and by Biotransfusion under the name "Biocol". The glue is a concentrated solution of fibrinogen (70–140 mg/ml) containing factor XIII and fibronectin, whose polymerization is induced by a solution of thrombin (4 to 400 International Units) in an extemporaneous mixture. The fibrinogen subsequently undergoes polymerization to form fibrin, forming a coagulum which brings about the adhesion of contacted tissues.

The major problems and difficulties raised by this product and its components are on the one hand the absence of complete characterization and reproducibility of the quantity of each of the components in the fibrinogen solution (factor XIII, fibronectin, aprotinin); and on the other hand the difficulty of absolute viral inactivation of such a product with regard to non-enveloped viruses such as unconventional transmissible agents. This has placed a limitation on the possibility of widespread use of such products in certain countries (for example the United States).

Finally, the European patent application published under the No. 0 466 383 (Bausch & Lomb Incorporated) has recently described an adhesive composition for surgical use consisting of crosslinked natural collagen, in which the fluidity and the concentration necessary on account of the intended surgical applications are regulated by the proportion of crosslinking in the collagen solution. According to this document, the desired fluidity and concentration are obtained by mixing a solution of highly crosslinked natural collagen and a solution of natural collagen having a lower degree of crosslinking. Biological tissues may be bonded applying the abovementioned mixture, heated beforehand so as to obtain a fluidity sufficient to enable its application to the tissues, then allowing it to cool.

However, this type of adhesive composition based on crosslinked collagen is difficult to handle and may give rise to problems with application because of the difficulties in making this composition sufficiently fluid. Indeed, the higher the proportion of crosslinked collagen, the greater the difficulty of reaching the degree of fluidity which is required for proper application to the biological tissues.

Moreover, the presence in this composition of collagen having a relatively low degree of crosslinking, although enhancing the fluidity of the mixture and thus the quality of application, places a limit on the mechanical strength.

It is in fact known that the mechanical strength and the biodegradability of collagen depend essentially on the degree of crosslinking and on the nature of the crosslinking brought about.

Moreover, European Patent Application No. 87 401 573.8 has disclosed a method of crosslinking collagen which makes it possible to crosslink the collagen in bulk and homogeneously without the covalent addition of a chemical molecule. Crosslinking is brought about by carrying out controlled oxidation of the collagen using a solution of periodic acid or sodium periodate at room temperature and in an acidic medium, then by continuing treatment at a basic or neutral pH. This method makes it possible to prepare insoluble, crosslinked collagen products (gels, films, powders, pellets or else bone filling products) which have good mechanical characteristics and good biodegradability, but is unsuitable for the preparation of fluid, liquid products.

The object of the invention is to provide a biocompatible, bioreserbable and non-toxic adhesive composition which is suitable for surgical use.

The object of the invention is also to provide an adhesive composition which is easy to use and can be injected, in particular, using needles or catheters, and which has the degree of fluidity required for proper application, especially to biological tissues, and which is stable over time while retaining its adhesive properties.

Another object of the invention is to provide an adhesive composition which makes it possible to obtain satisfactory adhesion in parallel with good mechanical resistance and biodegradability, with no risk of the release of toxic residues.

One other object of the invention is to provide a process for the preparation of such a composition, which is easy to carry out, and to provide adhesive kits for surgical use, which are practical and simple to use.

For this purpose, one subject of the invention is an adhesive composition based on non-crosslinked collagen which nevertheless is potentially crosslinkable.

The adhesive composition according to the invention is characterized in that it comprises a reactive acidic solution of non-crosslinked and potentially crosslinkable collagen or gelatin modified by oxidative cleavage.

Other subjects of the invention are reactive acidic solutions and powders based on non-crosslinked collagen or gelatin modified by oxidative cleavage, which are intermediate products for the preparation of the abovementioned adhesive compositions, and the process for their preparation.

The powder is a powder of non-crosslinked and potentially crosslinkable collagen or gelatin modified by oxidative cleavage which is soluble at an acid pH.

The process for its preparation is characterized in that it consists in:

preparing an acidic solution of collagen;

subjecting the said acidic aqueous solution at room temperature to controlled oxidation by a solution of periodic acid or one of its salts at a concentration of between approximately 1 and $10^{-5}$ M;

precipitating the oxidized and non-crosslinked collagen at an acidic pH; and isolating and concentrating, and then dehydrating, the said non-crosslinked collagen modified by oxidative cleavage so as to obtain it in the form of a reactive acidic powder.

The reactive acidic solution is a concentrated acidic solution of non-crosslinked collagen or gelatin modified by oxidative cleavage. It may be obtained either by concentration directly from the redissolved precipitate resulting from the periodic acid oxidation or from the powder according to the invention as defined above, after redissolution in water, at an acid pH.

The preferred process for its preparation is characterized in that it consists in:

preparing a sterile powder of non-crosslinked and potentially crosslinkable collagen or gelatin modified by oxidative cleavage, dissolving the required quantity of this powder in sterile water by heating at a temperature of between approximately 40° C. and 80° C.

Yet another subject of the invention comprises adhesive kits which are intended for surgical use. These kits are characterized in that they comprise:

a reactive acidic solution of non-crosslinked and potentially crosslinkable collagen or gelatin modified by oxidative cleavage;

a neutralizing solution; and mixing means for extemporaneous mixing of the said solutions.

They are present advantageously in the form of a double syringe equipped with a mixer.

A final subject of the invention is a method of application of an adhesive composition according to the invention to biological tissues and/or an implanted biomaterial, characterized in that it consists in:

bringing the reactive acidic solution of non-crosslinked collagen or gelatin modified by oxidative cleavage to a level of fluidity which is suitable for appropriate distribution on the said tissues and/or biomaterial;

extemporaneously mixing the reactive acidic solution with a neutralizing solution so as to obtain a pH of between 6 and 10;

applying the neutralized reactive mixture which has a suitable level of fluidity immediately, before crosslinking, to the biological tissues and/or implanted biomaterial to be bonded; and leaving the mixture to polymerize by crosslinking at the temperature of the human body.

The inventors have surprisingly discovered the potentially adhesive properties of oxidized collagen.

They have also discovered that, by carrying out in situ crosslinking of such a collagen, biological tissues can be bonded with one another or with an implanted biomaterial, this bond being of appropriate mechanical strength and biodegradability.

Finally, the inventors have discovered that non-crosslinked collagen modified by oxidative cleavage can be stored at an acid pH in the frozen state, for the purpose of extemporaneous preparation, this treatment making it possible to avoid the autocrosslinking of collagen while preserving its adhesive reactive properties.

According to the invention the term "collagen" relates equally to collagen or to gelatin resulting from a heating operation or any other method.

In addition, the invention provides an adhesive based on non-crosslinked, oxidized collagen which has undergone controlled heating and which is intended to be crosslinked in situ.

According to the invention, the term "to be crosslinked in situ" refers to the act of bringing about the crosslinking of the modified and reactive collagen after application to the biological tissues and/or diffusion into the said tissues.

This is counter to the teaching of the prior art, which recommends the application of ready-crosslinked natural collagen and which does not envisage an operation of covalent crosslinking, without the addition of crosslinking agent, after application to the biological tissues.

Oxidized collagen is obtained by treatment with periodic acid or one of its salts, which brings about cleavages within the said collagen and thus creates reactive sites.

This treatment is carried out on an acidic solution of collagen with a concentration of between 0.1 and 50 g/l. The collagen concentration is preferably 5 g/l.

The term "collagen" in this case denotes any type of collagen, whether of human or animal origin, such as, for example, enriched human collagen of type I, human collagen of type III, also enriched, human collagen of type I+III or of type IV or else animal collagen of type I or of type I+III.

The collagen in an acidic medium is subjected to the action of periodic acid or one of its salts by mixing it with a solution of the said acid or one of its salts at a concentration of between 1 and $10^{-5}$ M, preferably between $5 \times 10^{-3}$ M and $10^{-1}$ M.

The reaction is carried out at room temperature for a period of time which may range from 10 minutes to 72 hours and Which is preferably approximately 2 hours.

Controlled oxidation of the collagen is then carried out without bringing about the crosslinking thereof.

The invention additionally provides a means of isolating and preserving this intermediate product in the form of a powder or solution.

In fact, the addition of a salt, in particular sodium chloride, to the acidic solution obtained above brings about the precipitation of the oxidized collagen having reactive sites which are useful for the final crosslinking.

After a number of successive washing operations, resuspension in ethanol or acetone and dehydration under sterile conditions, oxidized collagen is obtained in the form of a powder. This powder is soluble in an acidic medium.

The dehydration may also be carried out by freeze-drying under sterile conditions in accordance with the well-known methods which are used industrially in this field.

According to another embodiment of the invention, a concentrated, reactive, acidic solution is obtained by concentration of the precipitate resulting from the periodic acid oxidation and redissolution of this precipitate under hot conditions or under vacuum in order to remove any organic solvents.

According to the invention, the powder or the concentrated solution of potentially reactive oxidized collagen may be prepared in a relatively large quantity and may be stored in this form in the frozen state. The storage temperature is chosen to be between approximately −10° C. and −80° C. These storage conditions are simple and make it possible, in addition, to maintain the reactivity of the modified collagen.

The powder and the concentrated acidic solution constitute intermediate products in the preparation of the adhesive composition according to the invention.

In accordance with the invention it is possible to prepare a reactive acidic solution from the non-crosslinked potentially crosslinkable oxidized collagen powder by dissolving it in an acidic medium.

In order to do this, the oxidized collagen powder is dissolved in sterile water heated to a temperature of between 40° C. and 80° C. This heating facilitates the dissolution of the oxidized collagen at relatively high concentrations which may range from 5 to 30% by weight.

The oxidized collagen is preferably incorporated gradually, for example in portions of 5% (weight/weight). It is advantageous to wait for virtually complete dissolution of each portion of powder before introducing the following portion.

The speed of incorporation may vary depending on the oxidized collagen powder; it generally takes between 10 minutes and 6 hours.

A homogeneous solution is thereby obtained.

According to the invention, the reactive acidic solution of non-crosslinked and potentially crosslinkable oxidized collagen is stored in the frozen state, preferably at a temperature of between −10° C. and −80° C. This reactive acidic solution is stable under these conditions. It constitutes an intermediate product for the preparation of an adhesive composition according to the invention.

This mode of preservation, besides the simplicity of its application, enables the reactivity of the collagen to be maintained until the time when its use is desired.

The crosslinking of the oxidized collagen at an acid pH is brought about by a simple change in pH to a neutral or basic value. For this purpose a buffer solution is used such that, after it has been mixed with the reactive acidic solution of oxidized collagen, the resulting pH is between 6 and 10. This solution consists advantageously of sodium phosphate or carbonate.

The invention therefore makes it possible to prepare adhesive kits which are intended for surgical use, for example for bonding tissues to one another or to an implanted biomaterial. This kit comprises a reactive acidic solution as described above, a neutralizing solution, and mixing means for extemporaneously mixing these two solutions. The kit is stored at a sub-zero temperature, preferably between −10° C. and −80° C., in order to preserve the reactivity of the oxidized collagen and its adhesive properties.

According to a preferred embodiment of the invention the kit is present in the form of a double syringe equipped with a mixer, one of which syringes contains the reactive acidic solution of oxidized collagen as described above while the other contains the neutralizing buffer, this double syringe preferably being frozen so that it can be stored and kept.

According to the invention, neutralization is advantageously carried out at the time of use before application of the reactive acidic solution of oxidized collagen to the biological tissues to be bonded and, if appropriate, the implanted biomaterial.

The time required for the crosslinking of the reactive mixture produced in this way from the reactive acidic solution and the neutralizing solution is sufficient to permit the application of this reaction mixture to the tissues and/or biomaterial before polymerization by crosslinking.

For proper application of the reactive neutralized mixture with good distribution of the latter over all of the tissues it is advantageous to render the said mixture sufficiently fluid. Thus the reactive acidic solution and the neutralizing solution which come, for example, from a kit as mentioned above are heated at a temperature of between 30° C. and 60° C., preferably from 42° to 50° C.

These two heated solutions are subsequently mixed using mixing means.

The neutralized reactive mixture is applied at this temperature immediately before crosslinking takes place to the biological tissues which are held in the correct position for the desired bond.

The composition is then allowed to act for several minutes to bring about crosslinking and the bonding of the tissues. The optional cooling is necessary neither for crosslinking nor for adhesion, but is imposed by the experimental conditions.

It is of course possible to apply the reactive neutralized mixture after having brought it to the body temperature of the patient or animal.

The mixture of the two abovementioned solutions which have been heated and applied to the tissues and/or to a biomaterial reacts rapidly, for example in a few minutes, to form an adhesive gel which bonds the tissues to one another or to the implanted biomaterial. The crosslinking time is of course variable as a function, in particular, of the level of oxidation of the collagen, of the concentration of the reactive acidic solution of oxidized collagen, of the reaction temperature, of the pH of the mixture, etc. In particular, the reaction is accelerated by increasing the temperature or by employing a more alkaline pH of higher than 8.

According to other embodiments of the invention it is possible to consider applying the reactive acidic solution, for example to the skin, in the form of a spray and then to allow neutralization to take place by means of the medium, in this case the skin, especially when rapidity of action of the composition is not an essential requirement.

It is also possible to consider introducing the reactive acidic solution into the body of the patient or the animal using catheters and, similarly, to allow neutralization to take place by means of the organic medium itself. However, it is of course also possible to consider introducing the reactive mixture with the aid of catheters, especially if the desired effect is to be obtained very rapidly.

The adhesive material obtained according to the invention has good mechanical characteristics owing, in particular, to homogeneous crosslinking in bulk throughout the tissues, but also is of good biodegradability.

Moreover, it is not toxic, because the modification of the collagen does not occasion the addition of a foreign chemical agent which might be released later on and might constitute the origin of some degree of toxicity.

The compositions and products according to the invention have a number of areas of interest in surgery because of their adhesive properties. Each area and each different application makes use of different functions such as, in particular, adhesion, haemostasis, leaktightness (with respect to liquid or to gas), cicatrization, filling, prevention of instances of adhesion in surgery, embolization, a local system for the release of medicamentary active principles, etc.

The reactive acidic solution is a fluid product which is able to interpenetrate the anfractuosities of the biological tissues to which it is applied and enables the formation, after crosslinking, of a gel which is capable of holding tissues which have been placed side by side, in particular with the aim of adhesion and of definitive cicatrization. Moreover, one of the biological tissues may be replaced by a biomaterial such as a compress or a patch.

Adhesion is an intrinsic property which was discovered by chance, and the fluidity of the product to be applied derives advantageously from the monomeric molecular structure, which has as low as possible a degree of crosslinking and which is stable over time, of the reactive acidic solution, despite its potentially reactive and crosslinkable nature.

Therefore, the composition according to the invention may be used as a substitute, for example, for microsuture operations on nerves by holding the two ends of the damaged nerve, or else may be used for the adhesion of the two parts of the aortic tunics in the case of pathologies of acute dissection of the aortic arch.

The high degree of fluidity of the reactive acidic solution or of the reactive mixture according to the invention, its power to penetrate tissues and its susceptibility to crosslinking in situ also enable the adhesive composition according to the invention to be used with the aim of limiting the flow of blood, the flow of a liquid other than blood or the flow of a gas from one biological cavity to another or to the outside of the organism.

The adhesive material formed after crosslinking in situ of the oxidized collagen may constitute a mechanical barrier, in addition to the function which may also be fulfilled by the collagen molecule with regard to the initiation of the coagulation cascade.

These properties give the composition according to the invention a haemostatic role, and it may therefore be used for stopping bleeding from a biopsy, from an incision or from a section resulting from resection of the parenchyma of a highly vascularized organ (the liver, kidney or spleen) by application of the composition, on its own or in conjunction either with a compress or haemostatic product or with ligature techniques or those of conventional electrocoagulation. It may also be used for stopping bleeding or diffuse discharge from the surface of various tissues following partial resection, incision or trauma.

The composition according to the invention may also, for example, provide leaktightness in the case of curettage operations on the lymphatic system (lymphostasis), the leaktightness of anastomoses carried out by suture operations to join together two parts of organs or of viscera, in particular when one of these organs contains biological fluids (brain—dura mater, eye—cornea, digestive apparatus, vessel), the aim of this leaktightness being better cicatrization of the anastomosis in order to ensure permanent leaktightness of the tissues, making it possible to avoid fistulation (oesophageal, vascular or visceral anastomosis); or else the leaktightness of pulmonary anastomoses which is difficult to make leaktight to the pressure of gases.

The composition according to the invention provides a collagenic matrix which is itself devoid of toxic substances, in contrast to the GRF glue described above, for example, which is capable of being infiltrated by cells and vessels and can thus be gradually replaced by the endogenous conjunctive tissue. First of all, the crosslinked gel of oxidized collagen provides a matrix which adheres firmly to the underlying tissues and forms a mechanical barrier which therefore prevents any leak. Subsequently, the conjunctive tissue formed in situ and in the product according to the invention provides leaktightness and definitive repair.

The breakdown time, and therefore the primary cohesiveness, and the role in filling may be modified by way of the concentration of the collagen in the reactive acidic solution or by way of its oxidation, in particular in terms of the crosslink density.

The reactive acidic solution intrinsically provides, by way of its adhesive properties, the possibility of bonding one tissue to another or to a biomaterial, for example a collagen patch or a compress, and therefore makes it possible to complete the matrix which is necessary for the filling-in and cicatrization of damaged tissues.

The composition according to the invention may thus be applied to walls following the resection of a tumour or cyst, or may in particular be used for filling the cavities resulting from curettage operations or from resections of a tumour or cyst.

It may also be employed with the aim of definitive obstruction of the outlet of vessels from an organ or a tissue in order to suppress or limit the vascularization of the latter, in order to cause it to regress or disappear.

The composition according to the invention may thus be applied, in particular, to the embolization of cerebral arteriovenous malformations or of meningiomas or hepatic tumours.

In the field of the prevention of instances of adhesion in surgery, the composition according to the invention enables the damaged tissue to reform from a proper cicatrization base, which has the effect of limiting the subsequent appearance of instances of adhesion in surgery, that is to say of disorganized pathological tissue joins connecting two tissues or two organs to one another when they are naturally separated, by virtue of more careful haemostasis, better leaktightness and better separation of the tissue bases which it provides.

The composition according to the invention may also find application, in particular, in repair surgery of the tendons or in the leaktightness of digestive anastomoses in order to limit the appearance of instances of adhesion associated with an attempt at natural repair.

Moreover, the composition according to the invention may, in parallel with its adhesive properties, constitute a local system for release of medicamentary active principles.

In effect it constitutes a collagenic matrix which may be used as a reservoir for an active substance. This substance is then released in two phases: in a first phase, the portion of the active substance which is in the soluble phase in the interstitial fluid of the adhesive gel is released by fluid diffusion. In a second phase, the active substance, encased in or connected to the collagen molecules, is released in the course of the gradual breakdown of the matrix.

The invention may consequently be applied to the fields of general and digestive surgery, hepatic, gastric and pancreatic surgery, neurosurgery, urology and nephrology, obstetric and gynaecological surgery, ear, nose and throat surgery, craniofacial surgery, plastic and reconstructive surgery, cardiovascular surgery, pulmonary and thoracic surgery, and in ophthalmology, orthopaedics, dental and periodontic surgery, etc.

From reading the above it will be noticed that each function of the composition according to the invention is found in a number of fields and applications and, for each surgical application, a number of functions may be applied; nevertheless, these functions are ordered according to whether they are essential or complementary; the former result from the intrinsic properties of the composition, namely adhesiveness, biocompatibility, bioresorbability and lack of toxicity, and are predominant in the role of the composition according to the invention, regardless of the desired function; the latter result from the said basic properties.

The examples which follow illustrate the process for the preparation of a composition according to the invention and illustrate the isolation of the intermediate products for this preparation. They also illustrate a preferred embodiment of an adhesive kit according to the invention, as well as the adhesive properties of the composition according to the invention.

EXAMPLES

I—PREPARATION.

Example 1

Preparation of a non-crosslinked collagen powder modified by oxidative cleavage using periodic acid.

In order to prepare 20 g of powder, an acidic collagen solution is prepared by dissolving 20 g of pepsin-containing bovine collagen I (dry and free of ash) in 20 liters of 0.012 N hydrochloric acid, with stirring at a temperature of between approximately 4° C. and 8° C. for not less than 8 hours.

The solution is subsequently filtered under sterile conditions on a filter plate, and the filtrate is collected in a sterile flask.

4.1 liters of sterile sodium chloride (240 g/l) are then added to the filtrate with stirring, and stirring is continued for about 10 minutes. The sodium chloride solution and the filtrate are left in contact for not less than 8 hours.

The suspension is then transferred under sterile conditions into sterile centrifugation vessels. Centrifugation is carried out at approximately 8000 rpm for 15 minutes at about 15° C.

The precipitate is recovered in order to undergo controlled oxidation using periodic acid.

For this purpose the precipitate is taken up in sterile 0.012 N hydrochloric acid, adjusting the concentration of collagen to 0.5%. The mixture is stirred at a temperature of between approximately 4° C. and 8° C. for not less than 8 hours.

The temperature of the medium is then brought to approximately 20° C., and subsequently 80 ml of sterile 0.4 M periodic acid (365 mg) of periodic acid per gram of collagen) are added thereto with stirring.

Stirring is continued for about 2 hours in the absence of light, and then 0.8 liter of sterile sodium chloride (240 g/l) is added, continuing stirring for about 5 minutes more.

The suspension is allowed to stand for about 30 minutes and is then transferred to sterile centrifugation vessels. Centrifugation is then carried out at approximately 8500 rpm for 15 minutes at about 20° C.

The precipitate is recovered and is resuspended in 4800 ml (the required quantity) of sterile NaCl, 41 g/l, and sterile HCl, 0.012 N. Stirring is continued for about 1 hour and then the suspension is transferred to sterile centrifugation vessels and centrifugation is carried out at approximately 8500 rpm for 15 minutes at about 20° C.

The precipitate is recovered and a second washing operation is carried out in the same way as before.

The precipitate from this second washing operation is recovered and is resuspended as for the preceding washing operations.

The suspension is then stirred for not less than 8 hours at about 4°–8° C.

The suspension is subsequently transferred to centrifugation vessels and centrifugation is carried out at 8500 rpm for 15 minutes at 20° C.

The precipitate recovered is resuspended in a 90% solution of acetone in water.

The suspension is stirred for about 15 minutes and the precipitate is recovered by filtration on a nylon cloth.

The precipitate obtained is washed 3 times with 80% acetone and 3 times with 100% acetone.

The acetone-containing precipitate which results is dehydrated in a stream of sterile air until it reaches a constant point. A quantitative yield of close to 100% is obtained.

In order to store the oxidized collagen powder obtained, it is placed in sterile flasks which are frozen at −80° C.

Example 2

Preparation of a reactive acidic solution of non-crosslinked collagen modified by oxidative cleavage using periodic acid.

The required quantity of non-crosslinked, oxidized collagen powder is dissolved in sterile ultra-filtered water.

The quantity of powder ($P_p$) required for the preparation of 100 g ($P_s$) of reactive acidic solution is calculated as follows:

$$P_p = \frac{P_s \times c}{(100 - h)}$$

in which $P_s$ denotes the quantity of reactive acidic solution prepared, c represents the final concentration of collagen in the reactive acidic solution, and h denotes the residual humidity of the non-crosslinked, oxidized collagen powder.

The quantity of ultrafiltered water ($P_e$) is calculated as follows:

$$P_e = P_s - P_p$$

Therefore, for the preparation of 100 g of a 15% strength reactive acidic solution from a powder having a residual humidity of 14.5%:

$$P_p = 17.54 \text{ g and } P_e = 82.46 \text{ g}$$

For the preparation of 100 g of a 20% strength reactive acidic solution from the same powder:

$$P_p = 23.39 \text{ g and } P_e = 76.61 \text{ g}$$

In order to do this the temperature of the ultrafiltered water is adjusted to approximately 60° C. and the collagen powder obtained in accordance with Example 1 is added, with stirring, in portions of approximately one third each time. Between each addition, stirring is continued until a fluid solution is obtained.

On account of the controlled heating which is carried out, the collagen loses its helical structure and is converted to gelatin.

When all of the oxidized collagen powder has been added, stirring is continued until a slightly viscous, homogeneous solution is obtained.

In order to store the reactive acidic solution prepared in this way, it is placed in sterile flasks and frozen at −20° C.

Example 3

Preparation of an adhesive kit for surgical use.

For a kit in the form of a double syringe equipped with a mixer, a reactive acidic solution of non-crosslinked oxidized collagen, prepared in accordance with Example 2, is placed in one syringe and a buffer solution is placed in the other syringe.

There are 27.5 g of 0.41M sodium carbonate buffer per 100 g of 15% strength reactive acidic solution.

II—TEST OF IN VITRO REACTIVITY. The time required for the reactive acidic solution to crosslink and form a gel is measured under the following physiological use conditions:

1 g of 15% strength reactive acidic solution is heated at about 42° C. for 2 to 3 minutes;

275 microliters of 0.41M sodium carbonate buffer are added thereto;

the mixture is stirred with a spatula for about 15 seconds; and the appearance of the resulting product is noted every 60 seconds.

The results are as follows:

Step I: after 0.5 min: viscous appearance

Step II: after 1.5 min: semi-gel appearance

Step III: after 2.5 min: solid gel appearance

III—TEST OF ADHESIVENESS: EVALUATION EX VIVO

The evaluation of the adhesive properties of compositions according to the invention was carried out on rabbit back muscle tissues. These tissues are kept at 4° C. in physiological serum for not more than 48 hours. The rabbit tissue is cut in the direction of the fibres using an electric slicer (slice thickness: 2.5±0.5 mm) and then squares measuring 25 mm×25 mm are cut out from the slices obtained.

The tests are carried out on a conventional traction apparatus, for example of the type Adamel Lhomargy model DY34, fitted with a 100N force meter. This apparatus enables force-displacement curves to be obtained. It also makes it possible to obtain the maximum traction force ($F_{max}$), Young's modulus, and the energy employed can be calculated from the area below the curve.

In each type of test, two test specimens of rabbit tissue are fastened with the aid of a cyanoacrylic glue (for example that sold under the name "Loctite superglue", in liquid or gel form) to large, inert supports which are very rigid and are made of glass or cardboard. The tests are carried out after 3 minutes at a pressure of 1 or 4N.

The composition is applied to the tissues by means of a double-syringe application system at a rate of 600 µl per sample in accordance with Example 3, at a collagen concentration of 15%.

The following values are recorded after contact for 3 minutes:

a) with the adhesive composition at 4N:
a maximum mean adhesive force of 2.5N (±0.36); (n=3)
a mean adhesion energy of 10.1 mJ (±3.7); (n=3)

b) with the adhesive composition at 1N:
a maximum mean adhesive force of 3.2N (±1.7); (n=3)
a mean adhesion energy of 5.4 mJ (±3.3); (n=3)

c) with fibrin glue at 4N:
a maximum mean adhesive force of 2.5N (±1.6);
a mean adhesion energy of 3.8 mJ (±2).

These values show that the adhesive composition according to the invention gives adhesion values ex vivo which are at least equal to those of the fibrin glue employed as control.

IV—TEST OF IN VIVO ADHESIVENESS.

The adhesive power of the composition according to the invention is determined in vivo in a standardized skin-flap glueing model.

OFA or Sprague Dawley rats which have been anaesthetized and shaved beforehand are given two equal wounds on each flank relative to the median line of the vertebral column. The standard wound comprises three sides of 2 to 3 cm in length. The incisions are made on the head, back and tail sides of each flank, with the head incision being made about 13 cm from the end of the snout of the rat.

After the standard wound has been made, from 0.2 to 0.4 ml of composition according to the invention is applied to the wound by a double syringe application system; the flap of skin is then positioned and held in place by the operator for 1 to 2 minutes. The sides of the wound, held properly by the product according to the invention, then no longer become detached and remain firmly held. In the absence of product or in the presence of another type of collagen such as non-oxidized heated collagen, the sides of the wounds do not remain properly in place and the wound opens up again.

The contralateral wound is glued identically using fibrin glue (Tissucol or Biocol) which is used as the control product.

This test on the one hand characterizes the primary adhesiveness of the adhesive according to the invention, namely the effectiveness of glueing at the moment when it is put in place, which must allow the sides to be held in place:

In the pre-operational situation, it is observed after being held for 1 to 2 minutes by the operator;

In the post-operational situation, it is observed in the first two hours when the animal is anaesthetized and in the first two days when the animal is awake and moving.

In addition, the primary holding must be taken over by the normal cicatrization process of the tissues, leading to the definitive adhesion of the sides of the wound which is classified as secondary adhesiveness.

On the other hand this test characterizes the good holding of the glued sides which is observed after the animal wakes up and then at 24, 48 and 72 hours.

If the product does not allow a physiologically correct adhesion to be obtained, the flap of skin becomes detached and leads to opening of the wound.

If the product leads to correct primary and then secondary adhesion, the flap of skin remains properly attached and definitive cicatrization continues.

FIG. 1 illustrates the sequence of events which take place after application of the adhesive according to the invention.

A comparative test was carried out with fibrin glue:

During the test the number of sides of wounds which remain correctly glued is counted every day for 3 days.

The result is expressed in terms of the number of correctly glued wounds relative to the total number of wounds.

The two tables which follow show the results of two independent tests, one carried out with Tissucol as control and the other with Biocol as control.

The results show that the adhesion which is observed with the adhesive composition over 3 days is at least equal to the control glues Biocol and Tissucol.

In the absence of adhesive product, no wound remains correctly glued.

|  | Day 1 | Day 2 | Day 3 |
|---|---|---|---|
| ADHESIVE COMPOSITION EXAMPLE 3 | 49/51 | 44/51 | 34/51 |
| Tissucol | 51/51 | 46/51 | 39/51 |

Test on 17 rats.

|  | Day 1 | Day 2 | Day 3* |
|---|---|---|---|
| ADHESIVE COMPOSITION EXAMPLE 3 | 24/24 | 23/24 | 15/21 |
| Biocol | 17/24 | 16/24 | 15/21 |

Test on 8 rats (* 1 rat died on day 3; its death was unrelated to the product but prevented the observation of 3 sides).

This test therefore demonstrates that the adhesive according to the invention makes it possible to obtain a degree of adhesion which is just as satisfactory as that of fibrin glue.

We claim:

1. Non-crosslinked and potentially crosslinkable pepsin-treated collagen or gelatin powder modified by oxidative cleavage in an aqueous solution, which is soluble at an acidic pH and stable on storage at a temperature of below 0° C. and for a period of at least one month.

2. Powder according to claim 1, characterized in that it comprises collagen or gelatin oxidized using a solution of periodic acid or one of its salts at a concentration of between approximately 1 and $10^{-5}$M.

3. Powder according to claim 1, characterized in that it is stored at a temperature of below 0° C.

4. Powder according to claim 3, characterized in that it is stored at a temperature of between approximately –10° C. and –80° C.

5. Powder according to claim 1, characterized in that the collagen or gelatin is of human or animal origin.

6. Process for the preparation of a powder according to claim 1, characterized in that it consists in:

preparing an acidic solution of pepsin-treated collagen;

subjecting the said acidic aqueous solution at room temperature to controlled oxidation by a solution of periodic acid or one of its salts at a concentration of between approximately 1 and $10^{-5}$M;

precipitating the oxidized and non-crosslinked pepsin-treated collagen at an acidic pH; and isolating and concentrating, and then dehydrating, the said non-crosslinked pepsin-treated collagen modified by oxidative cleavage so as to obtain it in the form of a reactive acidic powder;

freezing and storing the obtained reactive acidic powder at a temperature of below 0° C.

7. Process according to claim 6, characterized in that the oxidized and non-crosslinked collagen is precipitated at an acidic pH by addition of a salt, in particular by addition of sodium chloride.

8. Process according to claim 6, characterized in that collagen of human or animal origin is used.

9. Concentrated reactive acidic solution of non-crosslinked and potentially crosslinkable pepsin-treated collagen or gelatin modified by oxidative cleavage, substantially free from iodine or iodine derivatives and which is stable for a period of time of at least one month on storage at a temperature of below 0° C., to form an adhesive composition.

10. Reactive acidic solution according to claim 9, characterized in that it is prepared from a non-crosslinked and potentially crosslinkable pepsin-treated collagen or gelatin powder modified by oxidative cleavage by dissolution in water at an acidic pH.

11. Solution according to claim 9, characterized in that the concentration of collagen or gelatin is between approximately 5 and 30% by weight.

12. Solution according to claim 9, characterized in that it is stored at a temperature of below 0° C.

13. Solution according to claim 9, characterized in that it is stored at a temperature of between approximately –10° C. and –80° C.

14. Process for the preparation of a stable reactive acidic solution according to claim 10, characterized in that it consists in:

preparing a sterile powder of non-crosslinked and potentially crosslinkable pepsin-treated collagen or gelatin modified by preparing an acidic solution of pepsin-treated collagen, subjecting the said acidic aqueous solution at room temperature to controlled oxidation by a solution of periodic acid or one of its salts at a concentration of between approximately 1 and $10^{-5}$M, precipitating the oxidized and non-crosslinked pepsin-treated collagen at an acidic pH, and isolating and concentrating, and then dehydrating, the said non-crosslinked pepsin-treated collagen modified by oxidative cleavage so as to obtain it in the form of a reactive acidic powder, dissolving the required quantity of this powder in water by heating at a temperature of between approximately 40° C. and 80° C., cooling and storing the obtained reactive acidic solution at a temperature of below 0° C.

15. Process according to claim 14, characterized in that the non-crosslinked collagen or gelatin powder modified by oxidative cleavage is dissolved in sterile water in a proportion of approximately 5% (weight/weight).

16. Biocompatible, bioresorbable and non-toxic adhesive kit intended for surgical use for the bonding, in particular, of biological tissues to one another or to an implanted biomaterial, characterized in that it consists of:

a reactive acidic solution of non-cross-linked and potentially crosslinkable pepsin-treated collagen or gelatin modified by oxidative cleavage, and substantially free from iodine or iodine derivatives stored at a temperature of below 0° C.;

a neutralizing solution; and mixing means for extemporaneous mixing of the said solutions.

17. Kit according to claim 16, characterized in that the reactive acidic solution is a concentrated reactive acidic solution of non-crosslinked and potentially crosslinkable collagen or gelatin modified by oxidative cleavage.

18. Kit according to claim 16, characterized in that the reactive acidic solution is stored at a temperature of below 0° C.

19. Kit according to claim 18, characterized in that the reactive acidic solution is stored at a temperature of between approximately −10° C. and −80° C.

20. Kit according to claim 16, characterized in that the reactive acidic solution is obtained by preparing a sterile powder of non-crosslinked and potentially crosslinkable pepsin-treated collagen or gelatin modified by preparing an acidic solution of pepsin-treated collagen;

subjecting the said acidic aqueous solution at room temperature to controlled oxidation by a solution of periodic acid or one of its salts at a concentration of between approximately 1 and $10^{-5}$M;

precipitating the oxidized and non-crosslinkable pepsin-treated collagen at an acidic pH; and isolating and concentrating, and then dehydrating, the said non-crosslinked pepsin-treated collagen modified by oxidative cleavage so as to obtain it in the form of a reactive acidic powder; and dissolving the required quantity of this powder in water by heating at a temperature of between approximately 40° and 80° C.

cooling the obtained reactive acidic solution at a temperature of below 0° C.

21. Kit according to claim 16, characterized in that the neutralizing solution is a buffer which makes it possible to obtain, after mixture with the reactive acidic solution, a pH of between approximately 6 and 10.

22. Kit according to claim 21, characterized in that the said buffer consists of sodium phosphate or sodium carbonate.

23. Kit according to claim 16, characterized in that it is present in the form of a double syringe equipped with mixing means, one of which syringes contains the reactive acidic solution of non-crosslinked and potentially crosslinkabled pepsin-treated collagen or gelatin modified by oxidative cleavage, while the other contains the neutralizing solution, said double syringe being frozen or refrigerated at a temperature of below 0° C.

24. Method according to claim 19, wherein the reactive acidic solution is heated to approximately 37° C.

25. Method according to claim 19, wherein the neutralizing solution is a sodium phosphate or sodium carbonate buffer.

26. Method of bonding biological tissues to one another and/or to a biomaterial, comprising:

preparing a stable acidic solution of non-crosslinked and potentially crosslinkable pepsin-treated collagen or gelatin modified by oxidative cleavage, according to claim 16;

storing said stable solution at a temperature of below 0° C.;

heating said stable stored solution to a temperature of between approximately 30° C. and 60° C. to obtain a level of fluidity which is suitable for appropriate distribution on the said tissues and/or biomaterial;

extemporaneously mixing the acidic solution of collagen or gelatin with a neutralizing solution so as to obtain a pH of between 6 and 10;

applying the neutralizing reactive mixture which has a suitable level of fluidity immediately, before crosslinking, to the biological tissues and/or biomaterial to be bonded; and leaving the mixture to polymerize by crosslinking at the temperature of the human body.

* * * * *

UNITED STATES PATENT AND TRADEMARK OFFICE
CERTIFICATE OF CORRECTION

PATENT NO.　：　5,618,551
DATED　　　：　April 8, 1997
INVENTOR(S)：　TARDY ET AL

It is certified that error appears in the above-indentified patent and that said Letters Patent is hereby corrected as shown below:

Column 16, line 7, change "24" to --25-- and "according to claim 19" to --according to claim 24--

Column 16, line 9, change "25" to --26-- and "according to claim 19" to --according to claim 24--

Column 16, line 12, change "26" to --24--

Signed and Sealed this

Eighteenth Day of May, 1999

Attest:

Q. TODD DICKINSON

*Attesting Officer*　　Acting Commissioner of Patents and Trademarks